United States Patent [19]
Henson et al.

[11] 4,041,760
[45] * Aug. 16, 1977

[54] EXERCISE APPARATUS

[75] Inventors: Glen E. Henson; Milton W. Fisher, both of Independence, Mo.

[73] Assignee: Robar Mini-Gym, Inc., Independence, Mo.

[ * ] Notice: The portion of the term of this patent subsequent to July 29, 1992, has been disclaimed.

[21] Appl. No.: 558,227

[22] Filed: Mar. 14, 1975

Related U.S. Application Data

[63] Continuation of Ser. No. 375,938, July 2, 1973, Pat. No. 3,896,672.

[51] Int. Cl.$^2$ .............................................. G01L 5/02
[52] U.S. Cl. ...................................... 73/379; 272/128
[58] Field of Search .......................... 73/379, 380, 381; 272/79 R

[56] References Cited

U.S. PATENT DOCUMENTS

| | | | |
|---|---|---|---|
| 2,199,955 | 5/1940 | Kruck | 73/381 |
| 3,640,530 | 2/1972 | Henson et al. | 73/379 |
| 3,896,672 | 7/1975 | Henson et al. | 73/379 |

Primary Examiner—James J. Gill
Assistant Examiner—Anthony V. Ciarlante
Attorney, Agent, or Firm—Lowe, Kokjer, Kircher, Wharton & Bowman

[57] ABSTRACT

An exercise apparatus providing for accommodating resistance while allowing the level of resistance to the exercise force to be varied is provided by the present invention. The exercise apparatus also includes a movable arm for indicating the magnitude of the force exerted by a user of the apparatus. A frictional member is journaled on a rotatable shaft which is rotated by a user of the apparatus. This frictional member is sandwiched between two other members rotatably coupled with the shaft and engageable with the first member to create frictional resistance. Means is provided for moving one of the members a predetermined distance longitudinally of the shaft in the direction of the frictional member and for holding the member in a predetermined longitudinal position to cause it to grip the frictional member with a predetermined force. Centrifugal force responsive structure is also provided and is coupled with the other member which sandwiches the frictional member. The centrifugal force responsive structure is responsive to the speed of rotation of the shaft and is capable of moving the member in the direction of the frictional member for engagement with the latter with increasing force as increases and for withdrawing the sandwiching member from the frictional member as the speed of rotation decreases. The arm for indicating the magnitude of the force exerted by a user of the apparatus is coupled with the frictional member and holds the member against rotation with the shaft while accommodating a limited degree of pivotal movement.

20 Claims, 8 Drawing Figures

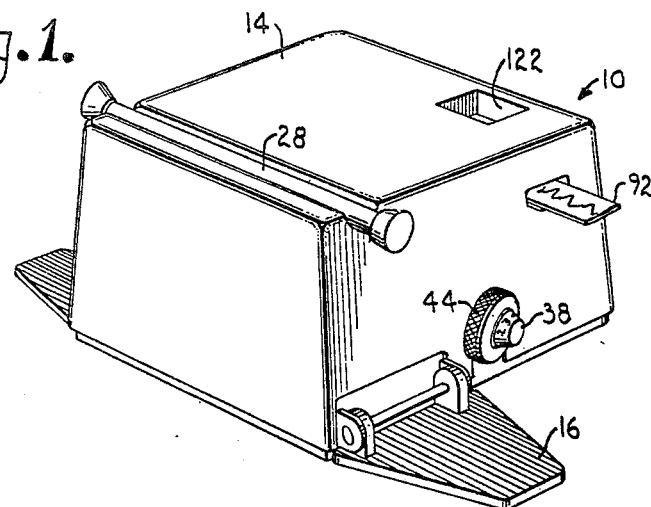
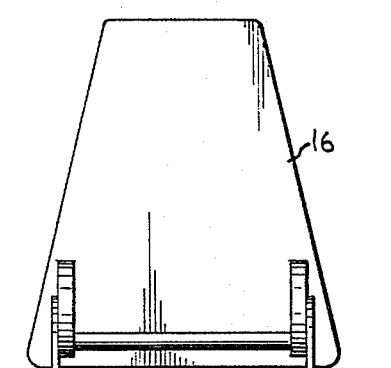
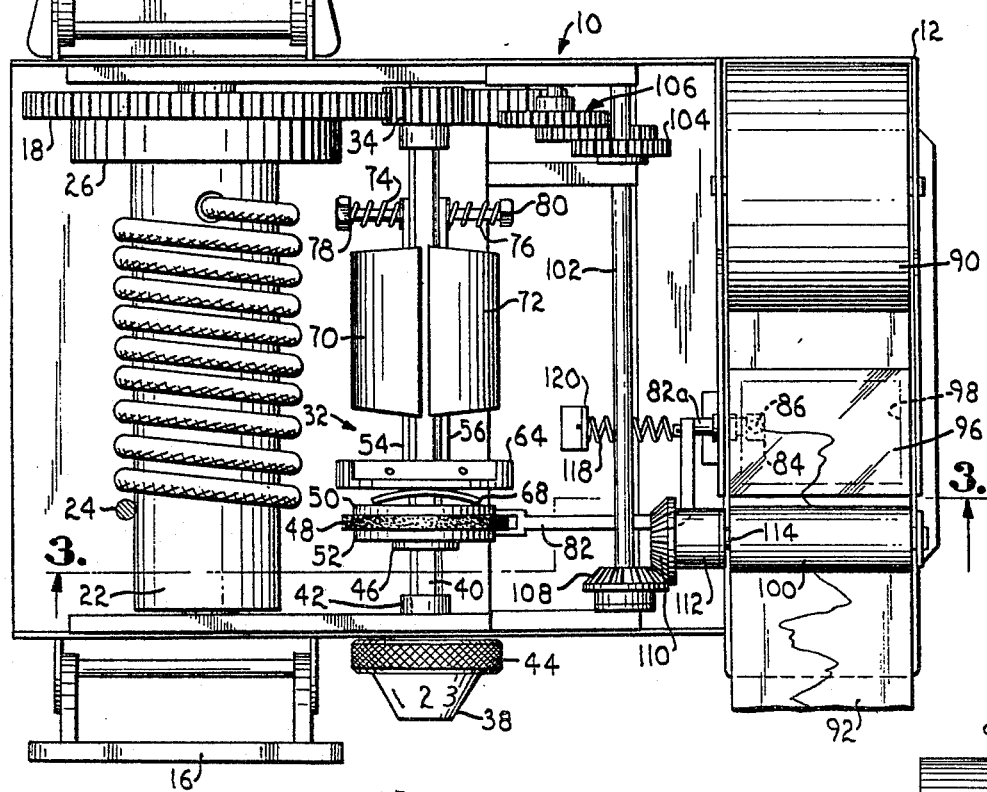
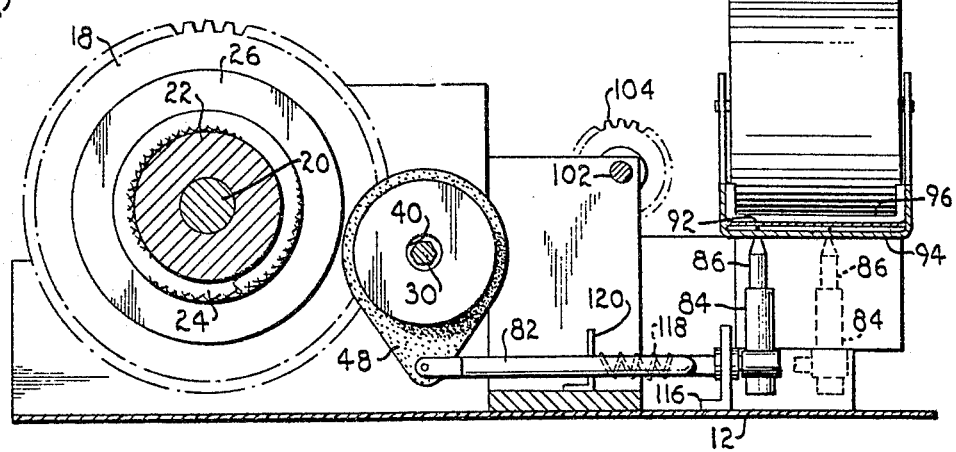

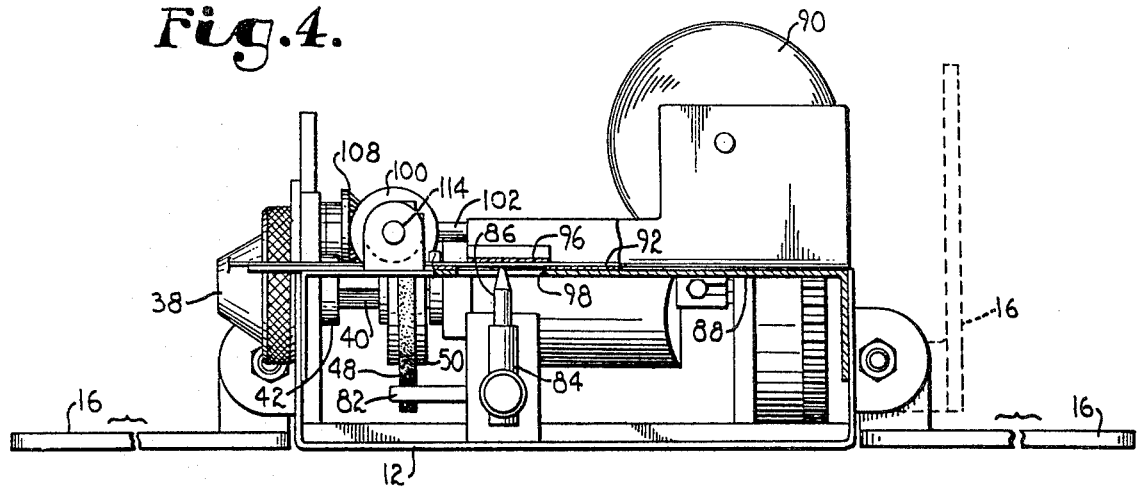
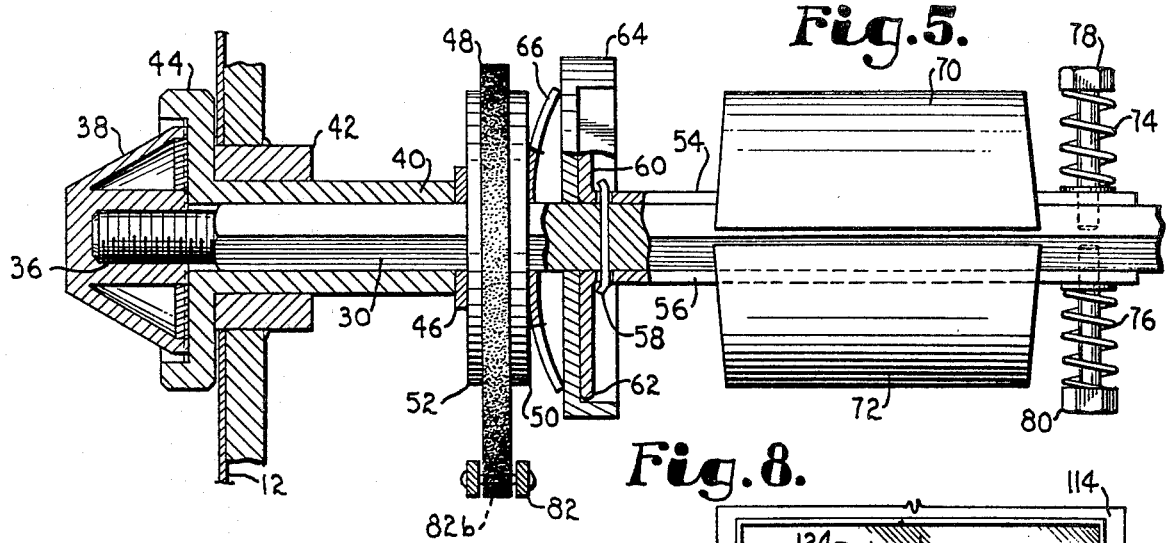
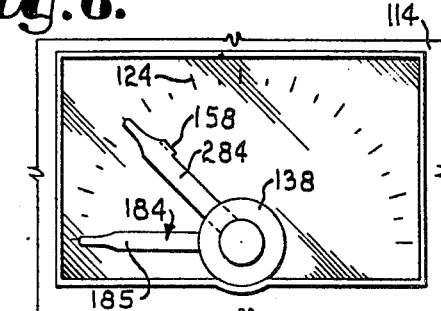
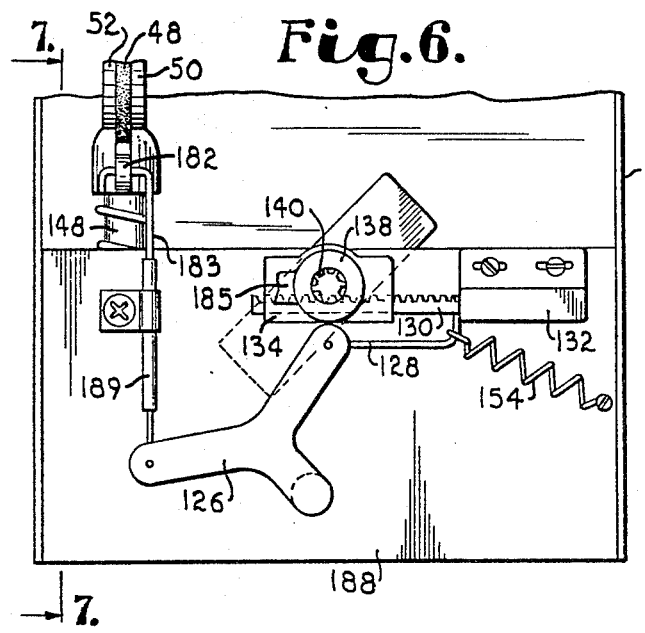
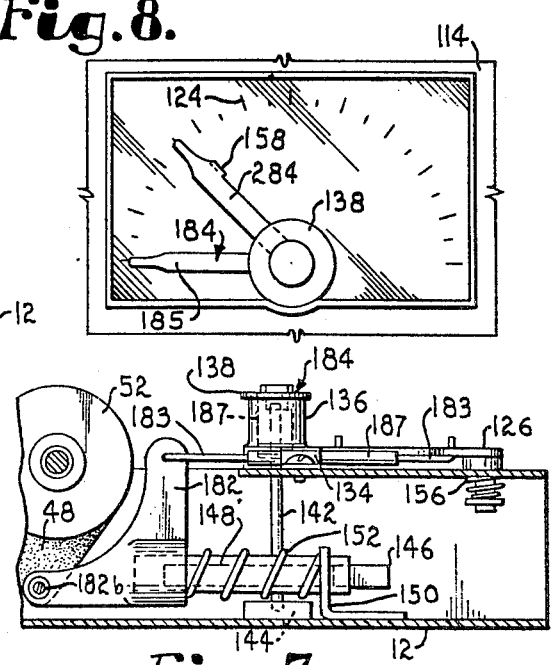

EXERCISE APPARATUS

This is a continuation of application Ser. No. 375,938, filed 7-2-73, now U.S. Pat. No. 3,896,672.

This invention relates to exercising apparatus generally, and more particularly to apparatus which provides for accommodating resistance and structure for indicating the magnitude of force exerted by a user of the apparatus.

This invention is an improvement in exercise apparatus of the type disclosed in U.S. Pat. No. 3,640,530, issued Feb. 8, 1972. This patent is expressly incorporated herein by reference to the extent necessary to obtain a full and complete understanding of the present invention.

A general discussion of isotonic and isometric exercises as well as isokinetic exercises which can be performed with the apparatus of the present invention are discussed in the above-referenced patent. There has been a definite need in isokinetic exercisers for a device which can vary the resistance level by a predetermined amount to accommodate persons of greatly varying strength.

While the isokinetic exercise apparatus disclosed in the above-referenced patent provides for some degree of measuring the force exerted by a user of the apparatus, such a measuring device has depended upon movement of the entire framework of the exerciser which has proved to be a relatively expensive construction.

It is therefore an object of the present invention to provide isokinetic exercise apparatus wherein the accommodating resistance may be adjusted to different predetermined minimum resistance levels thus offering a greater range than is possible with prior art devices having a non-variable accommodating resistance.

As a corollary to the above object, an objective of the invention is to provide a variable accommodating resistance which can offer greatly increased resistance potential utilizing only a single frictional member as a result of the member being sandwiched between two relatively movable members both having surfaces engageable with the frictional member.

As still another corollary to the object second above, an aim of this invention is to provide an isokinetic exerciser wherein the resistance level of the accommodating resistance may be preset simply by turning a knob located conveniently for a user of the apparatus.

Another important aim of this invention is to provide an isokinetic exerciser having an arm for indicating the force exerted by a user of the apparatus wherein the indicator arm does not depend upon movement of the supporting framework to provide the necessary indication.

Another objective of this invention is to provide an isokinetic exerciser wherein the accommodating resistance is provided by a frictional member engageable with centrifugal force responsive means and including an arm for indicating the amount of force exerted by a person using the exerciser wherein the arm is coupled directly with the frictional member to provide for increased accuracy as well as simplified construction.

Another one of the objects of this invention is to provide an isokinetic exerciser having an arm for indicating the amount of force exerted by a user of the apparatus and wherein a continuous graphic record of the force is made on a length of paper which is continually advanced throughout the exercise movement.

Referring now to the accompanying drawings:

FIG. 1 is a perspective view of the isokinetic exercise apparatus of the present invention showing the relative locations of the adjustable resistance control and the continuous graphic record of force exerted;

FIG. 2 is an enlarged, top plan view of the exercise apparatus with the covering case removed;

FIG. 3 is a horizontal cross-sectional view of the exercise apparatus taken along line 3—3 of FIG. 2;

FIG. 4 is a rear elevational view of the apparatus as shown in FIG. 2;

FIG. 5 is a greatly enlarged top plan view of the accommodating resistance mechanism of the invention with portions being shown in cross section to reveal details of construction;

FIG. 6 is a fragmentary top plan view of the exercise apparatus illustrating an alternative form of indicator arm;

FIG. 7 is a fragmentary horizontal cross-sectional view taken along line 7—7 of FIG. 6; and FIG. 8 is a fragmentary top plan view of the calibrated dial which is used in conjunction with the alternative form of indicator arm as shown in FIGS. 6 and 7.

Referring initially to FIGS. 1 and 2, the exercise apparatus of the present invention is designated generally by the numeral 10. Apparatus 10 comprises a supporting framework 12 of generally U-shaped cross-sectional configuration, as is most readily apparent from viewing FIG. 4. The framework 12 provides a supporting base for the working mechanism of the apparatus as well as for an external covering case 14. A pair of foldable foot rests 16 are hingedly coupled with framework 12 and the same may be moved from a position in planar alignment with the supporting base of framework 12 to a folded position adjacent the sidewall of carrying case 14 as indicated in FIG. 2.

A relatively large externally toothed drive gear 18 is pinned to a shaft 20 which is rotatably supported by framework 12. Also keyed to shaft 20 is a spool 22 around which a rope 24 is coiled. One end of the rope is rigidly secured to the spool. At the end of spool 22 adjacent gear 18 an annular dish-shaped housing 26 encloses a ratchet and pawl assembly (not shown). The ratchet and pawl assembly is described in detail in the above-referenced patent and permits the direction of rotation of spool 22 to be reversed under the influence of a coil spring (not shown) without turning gear 18 in reverse. Manifestly, the free end of rope 24 is secured to a handle 28 which is normally disposed outside of case 14 where it can be easily grasped by a user of the apparatus.

Also rotatably mounted on framework 12 in parallel relationship to spool 22 is an externally polygonal shaft 30 which mounts accommodating resistance mechanism designated generally by the numeral 32. One end of shaft 30 carries a gear 34 which is coupled for rotation with the shaft and is operably engaged with the relatively large drive gear 18. As illustrated in FIG. 5, the other end of shaft 30 is provided with threads 36 for mounting a complementally threaded adjusting knob 38. An elongated sleeve 40 has an internal surface complemental to the polygonal surface of shaft 30 and rotatably mounts the shaft within a bushing 42 carried by the supporting framework. The end of sleeve 40 adjacent knob 38 is flared outwardly into an annular projection 44 which complementally receives knob 38. The opposite end of sleeve 40 terminates in an integral flange 46.

A first frictional member 48 is journaled on shaft 30 and presents first and second frictional surfaces sandwiched between second and third members in the form of discs 50 and 52 which are coupled for rotation with the shaft 30. The centrifugal force responsive mechanism for increasing the frictional resistance between members 40, 48, 50 and 52 in direct relationship to the force exerted by a user of the apparatus comprises first and second elongated levers 54 and 56 disposed on opposite sides of shaft 30 and keyed to the latter by a common pin 58. Each lever 54 and 56 has an integral outturned end 60 and 62 respectively for bearing against a block 64 that is rotatably coupled with shaft 30 while being movable longitudinally of the latter. First and second leaf strips 66 and 68 are interposed between block 64 and disc 50 and are also rotatably coupled with shaft 30.

Disposed along the length of levers 54 and 56, and rigid therewith, are weights 70 and 72 respectively. Each of the weights has a cutaway portion of a general configuration complemental to the shaft 30 so as to partially surround the latter. Outward movement of levers 54 and 56, in response to centrifugal forces when shaft 30 rotates, is resisted by coil springs 74 and 76 respectively which are pinned to shaft 30 by bolts 78 and 80 respectively.

As shaft 30 rotates and member 50 grasps frictional member 48 with increasing force, the latter is prevented from rotating with the shaft by a link 82 which couples frictional member 48 with an indicator arm 84 which carries a marking instrument 86. Indicator arm 84 and its associated mechanism will now be described in greater detail. Disposed at the end of framework 12 opposite spool 22 is an elevated platform 88 which mounts a roll of translucent marking paper 90. A length 92 of the paper roll 90 is threaded between a generally U-shaped trough 94 and a transparent backing plate 96 (FIG. 3). A window 98 in the trough 94 allows marking instrument 86 to mark on the paper with support from backing plate 96. Adjacent the free end of the length of paper 92 is a friction roller 100 which is rotatably mounted on platform 88 and is in frictional engagement with the paper as it bears against trough 94.

A rod 102 extending parallel to shaft 30 is rotatably mounted by framework 12 and is provided with a drive gear 104 adjacent one end. Gear 104 is operably coupled with a reduction gear train 106 which in turn is operably engaged with gear 34 on shaft 30. The opposite end of rod 102 is provided with a bevel gear 108 that is operably engaged with a second bevel gear 110 for driving roller 100 through an integral spool 112 and associated drive shaft 114. Link 82, previously described, is of generally L-shaped configuration and has an extension 82a projecting perpendicular to the shorter leg of the link for mounting arm 84. Projection 82a is journaled in a tab support 116 rigid with supporting framework 12. A coil spring 118 has one end coupled with link 82 and the other end secured to an upwardly projecting bracket 120 so as to resist movement of link 82 under the influence of frictional member 48. Manifestly, while link 82 prevents rotation of the member with shaft 30, a limited degree of pivotal movement is accommodated which movement is utilized to measure the force exerted by a user of the exercise apparatus.

When a user of the apparatus 10 positions his feet on foot rests 16 and pulls on handle 28, shaft 30 is rotated at a speed proportional to the force exerted by the exerciser. Accordingly, levers 54 and 56 with weights 70 and 72 thereon will move outwardly to a greater extent in response to centrifugal forces as the speed of rotation of the shaft increases. As levers 54 and 56 move outwardly they force member 50 into tighter and tighter engagement with member 48 to thereby increase the frictional resistance between the members. To this end, knob 38 has been screwed on the shaft 30 a predetermined distance to cause sleeve 40 to move longitudinally of the shaft and member 52 to engage member 48 with a predetermined force. Thus, the minimum level of resistance offered by the exercise apparatus is determined by the extent to which knob 38 is screwed onto shaft 30. The frictional resistance between the members will continue to increase beyond this predetermined minimum level as member 50 grasps member 48 within increasing force in response to movement of lever arms 54 and 56. It is to be emphasized that rather than simply providing an adjustment for moving frictional member 48 closer to member 50, the sleeve 40 in cooperation with knob 38 actually provides for twice the braking action at the very outset of the exercise movement by virtue of the fact that member 52 rotates with shaft 30 while being in engagement with member 48. The magnitude of the minimum frictional resistance level may be increased even above twice what has heretofore been possible by screwing knob 38 still further onto shaft 30.

Springs 74 and 76 assure return of levers 54 and 56 to their at rest positions as the speed of rotation of shaft 30 is slowed. This, in turn, assures that contact between frictional member 48 and member 50 will be broken when desired.

While link 82, which is coupled with member 48 by a pin connection 82b holds the frictional member against rotation with shaft 30, a limited degree of pivotal movement is accommodated. This pivotal movement is translated to indicator arm 84 through link 82 and marking instrument 86 records the movement on length 92 of the roll of paper 90. Manifestly, member 48 can move only when the person exercising overcomes the frictional resistance between this member and members 50 and 52. Thus, the limited degree of pivotal movement of member 48 will be directly proportional to the force exerted by the person exercising. Since paper 90 is translucent in nature and backup plate 96 is transparent, a person exercising may observe the continual graphic recording of the force they are exerting through an opening 122 in case 14. Roller 100, which is driven through gear train 106, rod 102, and gears 108 and 110 continues to unroll paper 90 throughout the exercise movement to provide a continual recorded graph of exerted force. Movement of link 82 is always away from coil spring 118 which assures that arm 84 will be returned to its at rest position as pivotal movement of member 48 ceases.

Referring now to the alternative embodiment of the invention shown in FIGS. 6-8, construction of this alternative embodiment is, in every respect, identical to the construction of the embodiment described above with the exceptions noted hereinafter. A modified case 114 encloses the accommodating resistance mechanism of the apparatus and is provided with a dial 124 calibrated in units of force which is readily visible to a person exercising with the apparatus. An indicator arm 184 has a hand portion 185 which moves along the face of dial 124 to indicate to a person exercising the magnitude of force exerted. Arm 184 is coupled with frictional member 48 through an integral depending shank portion 187 and associated linkage as will now be described.

A first, generally L-shaped link 182 has one end secured to frictional member 48 by a nut and bolt assembly 182b or other appropriate connector. The opposite end of link 182 is coupled with a second elongated link 183 which moves within a sleeve 189 mounted on a supporting platform 188. Link 183 is, in turn, coupled with one end of a bell crank 126 pivotally mounted on platform 188. The other end of the bell crank is coupled with a third link 128 which is operably connected with a gear track 130. Gear track 130 is reciprocable back and forth between two spaced apart housings 132 and 134 which receive opposite ends of the gear track.

As illustrated in FIG. 7, housing 134 extends upwardly to present a collar 136 that receives shank portion 187 of arm 184. An integral washer 138 on arm 184 provides a bearing surface and seats shank portion 187 within collar 136. Rigid with the lowermost end of shank portion 187 is an externally toothed gear 140 which is operably engaged with gear track 130.

Shank portion 187 is provided with a central bore of a size to tightly receive the end of an upright pivot rod 142. Thus, pivot rod 142 will turn with arm 184 and, to this end, the lowermost end of rod 142 is rotatably mounted in a bushing 144. Rigid with pivot rod 142 is a counterweight 146.

The lowermost portion of L-shaped link 182 is of a greater cross-sectional dimension than either of the two ends of the link and is hollowed out to receive an elongated extension 148 which projects outwardly from the link and has its far end slidably received by a bracket 150 supported by framework 12. Extension 148 thus provides a guide for link 182 and a coil spring 152 resists movement of the link under the influence of frictional member 48. A second spring 154 coupled with third link 128 and a thrid spring 156 coupled with bell crank 126 cooperate with the spring 152 to assure return of arm 184 to its at rest position.

Again referring to dial 124, it is seem that a second indicator arm 284 is pivotally mounted on the face of the dial. This second arm is freely and independently pivotal through an arc of 180° and, as a result of a tab projection 158, arm 284 is carried by arm 184.

The modified structure of the exercise apparatus, as above described, is utilized to provide a user of the apparatus with an indication of the force exerted rather than utilizing roll of paper 90 to provide a continuous graph of the force. Thus, as member 48 moves a limited degree as the exercise force increases, arm 184 will move along the face of dial 124 to indicate to the exerciser the amount of force exerted. Arm 284 will be carried by the arm 184 to the position of the maximum force exerted where it will remain until reset at the end of the exercise. Counterweight 146 assures smooth movement of the arm 184 and minimizes "hunting" of the arm as a result of small variations in the force exerted.

Having thus described the invention, we claim:
1. Exercise apparatus comprising:
a rotatable shaft;
a first member having first and second frictional surfaces, said member being journaled on the shaft;
means for holding said first member against rotation with the shaft;
a second member coupled with the shaft and movable toward and away from said first surface for engagement with the latter upon rotation of the shaft;
a third member rotatably coupled with the shaft on the side of said first member opposite said second member and movable longitudinally of the shaft into engagement with said second surface whereby to sandwich said first member between the second and third members;
means for moving said third member a predetermined distance longitudinally of the shaft in the direction of said first member and for holding said third member in a predetermined longitudinal position whereby said third member grips said first member with a predetermined force;
means adapted to be acted upon by a user of the apparatus for rotating said shaft; and
centrifugal force responsive structure rotatably coupled with said shaft and responsive to the speed of rotation of the shaft for first moving said second member in the direction of said first member to engage the second member against the first member with greater force as the speed of rotation continues to increase, and for withdrawing the second member from the first member as the speed of rotation decreases.

2. The invention of claim 1, wherein said means for moving said third member comprises a knob threadably received at one end of the shaft, a sleeve keyed to the shaft and movable longitudinally of the latter, said sleeve being movable into engagement with the third member as said knob is screwed further onto the shaft.

3. The invention of claim 2, said centrifugal force responsive means comprising first and second elongated levers rotatably coupled with said shaft and pivotable on the shaft, each lever having an end for moving said second member in the direction of the first member, and weight means carried by each lever respectively in position to effect outward pivoting of the levers responsive to centrifugal force during rotation of the shaft.

4. The invention of claim 3, wherein is provided biasing means disposed at the end of each lever opposite the pivot end, said biasing means being coupled with the shaft and disposed for resisting said outward pivoting.

5. The invention of claim 1, wherein is included a supporting framework for mounting said shaft, a movable arm for indicating the magnitude of force exerted by a user of the apparatus, and wherein said means for holding said first member comprises linkage means for coupling said first member with said arm and for accommodating a limited degree of pivotal movement of the first member; and further including yieldable means supported by the framework and disposed for resisting the pivotal movement of said first member.

6. The invention of claim 5, wherein is included a dial calibrated in units of force mounted on said supporting framework, said arm being disposed above the dial.

7. The invention of claim 6, said linkage means comprising: a first link secured to said first member, a bell crank pivotally mounted on said supporting framework, a second link coupling the first link with one end of said bell crank, a gear track mounted on the framework, a third link coupling the other end of said bell crank with said gear track; and wherein is included a gear rigid with said arm, said gear operably engaging said gear track; and spring means for resisting movement of the arm by said first member whereby to return the arm to its at rest position.

8. The invention of claim 5, wherein is included a roll of marking paper carried by said framework, said arm comprising a marking instrument for making a mark on the paper corresponding to the magnitude of the exerted force, a drive roller in engagement with a length of the paper; and a gear train for driving said roller in response to rotation of the shaft whereby a continuous running record of the magnitude of force exerted by the user is marked on the paper.

9. The invention of claim 8, said paper being translucent, and wherein is included a transparent backing plate rigid with said supporting framewotk for said paper immediately opposite said marking instrument, the latter being disposed beneath said plate whereby a user of the apparatus may observe the markings on said paper.

10. Exercise apparatus as set forth in claim 1, wherein is included a supporting framework for mounting said shaft; means for indicating the magnitude of force exerted by a user of the apparatus; and wherein said means for holding said first member comprises linkage means for coupling said friction member with said force indicating means and for accommodating a limited degree of pivotal movement of said friction member; and further including spring means supported by the framework and disposed for resisting pivotal movement of said friction member.

11. Exercise apparatus as set forth in claim 10, wherein said yieldable means comprises spring means and including a tensioning screw for each of said spring means to vary the yieldable resistance of the spring means.

12. Exercise apparatus comprising:
a supporting framework;
a rotatable shaft carried by the framework;
a first member journaled on the shaft and presenting a frictional surface;
a second member coupled with the shaft and movable toward and away from the frictional surface for engagement with the latter upon rotation of the shaft;
means adapted to be acted upon by a user of the apparatus for rotating said shaft;
centrifugal force responsive structure rotatably coupled with said shaft and responsive to the speed of rotation of the shaft for first moving said second member in the direction of said first member to engage the frictional surface with greater force as the speed of rotation continues to increase, and for withdrawing the second member from the first member as the speed of rotation decreases;
a dial calibrated in units of force mounted on said supporting framework;
a movable arm for indicating the magnitude of force exerted by a user of the apparatus, said arm being disposed above said dial;
a first link secured to said first member;
a bell crank pivotally mounted on said supporting framework;
a second link coupling the first link with one end of said bell crank;
a gear track mounted on the framework;
a third link coupling the other end of said bell crank with said gear track;
a gear rigid with said arm, said gear operably engaging said gear track;
spring means for resisting movement of the arm by said first member whereby to return the arm to its at rest position; and
yieldable means supported by the framework and disposed for resisting the pivotal movement of said first member.

13. The invention of claim 12, wherein is included a second arm for indicating the maximum value of force exerted by a user of the apparatus, said second arm being pivotally mounted on the dial face and positioned to be engaged by the first-mentioned arm whereby the latter moves the second arm to register the maximum force value.

14. The invention of claim 12, wherein said arm comprises a shank portion and a hand portion disposed perpendicular to the shank portion, the said shank portion presenting said gear, and wherein is included a counterweight coupled with said shank portion at the end of the latter opposite the hand portion for damping the movement of the arm.

15. The invention of claim 12, wherein is included a roll of marking paper carried by said framework, said arm comprising a marking instrument for making a mark on the paper corresponding to the magnitude of the exerted force, a drive roller in engagement with a length of the paper; and a gear train for driving said roller in response to rotation of the shaft whereby a continuous running record of the magnitude of force exerted by the user is marked on the paper.

16. The invention of claim 15, said paper being translucent, and wherein is included a transparent backing plate rigid with said supporting framework for said paper immediately opposite said marking instrument, the latter being disposed beneath said plate whereby a user of the apparatus may observe the markings on said paper.

17. The invention of claim 16, wherein is included a first gear rigid with said shaft, and said gear train comprises a plurality of reduction gears operably engaged with the first gear for driving said roller at a reduced speed relative to the speed of rotation of the shaft.

18. The invention of claim 17, wherein is included a trough supported by said framework for guiding said paper as the latter is unrolled, said drive roller being supported by the framework and bearing against said trough, and wherein is further included a rod operably coupled with one of said reduction gears and extending in the direction of the roller, said roller being provided with a first bevel gear rigid therewith, and a second bevel gear rigid with said rod and operably engaged with the first bevel gear for driving said roller.

19. Exercise apparatus comprising:
a rotatable shaft;
a frictional member journaled on said shaft and having opposed first and second frictional surfaces;
means for holding said frictional member against rotation;
a first bearing member mounted on said shaft on one side of said frictional member and movable longitudinally of the shaft toward and away from one of the surfaces of the frictional member for engagement with the latter;
a second bearing member mounted on said shaft on the side of said frictional member opposite said first bearing member;
means adapted to be acted upon by a user of the apparatus for rotating said shaft;
centrifugal force responsive structure rotatably coupled with said shaft and comprising first and second elongated levers mounted for pivotal movement relative to said shaft;
weight means carried by each lever respectively in position to effect outward pivoting of the levers responsive to centrifugal force during rotation of the shaft;

said levers being disposed to move said first bearing member in the direction of said frictional member in response to said outward pivoting movement;

yieldable means for each of the levers respectively disposed adjacent the ends of the lever which is farthest removed from the pivot point, said yieldable means biasing each of said levers against said pivotal movement; and means for moving said second bearing member a predetermined distance longitudinally of the shaft in the direction of said frictional member and for holding said second bearing member in a predetermined longitudinal position whereby said frictional member is sandwiched between said first and second bearing members upon movement of said first bearing member in the direction of said frictional member.

20. Exercise apparatus as set forth in claim 19, wherein said means for moving said other bearing member comprises a knob threadably received at one end of said shaft; a sleeve keyed to the shaft and movable longitudinally of the shaft, said sleeve being movable into engagement with the third member as said knob is screwed further onto the shaft.

* * * * *